United States Patent [19]

Suzuki et al.

[11] Patent Number: 5,049,391
[45] Date of Patent: Sep. 17, 1991

[54] LIPOSOME ENCAPSULATED HEMOGLOBIN

[75] Inventors: Kazuhiko Suzuki; Keisuke Sakaguchi, both of Shizuoka, Japan

[73] Assignee: Terumo Kabushiki Kaisha, Tokyo, Japan

[21] Appl. No.: 408,485

[22] PCT Filed: Feb. 26, 1988

[86] PCT No.: PCT/JP88/00208

§ 371 Date: Aug. 25, 1989

§ 102(e) Date: Aug. 25, 1989

[87] PCT Pub. No.: WO88/06437

PCT Pub. Date: Sep. 7, 1988

[30] Foreign Application Priority Data

Feb. 27, 1987 [JP] Japan .................. 62-42826
Feb. 27, 1987 [JP] Japan .................. 62-42827

[51] Int. Cl.⁵ .................. A61K 37/22; A61K 37/14
[52] U.S. Cl. .................. 424/450; 264/4.3; 264/4.6; 514/6
[58] Field of Search .................. 264/4.3, 4.6; 424/450; 516/6

[56] References Cited

U.S. PATENT DOCUMENTS 4,133,874 1/1979 Miller et al. .................. 424/38
4,681,582 7/1987 Yamamoto .................. 604/890
4,776,991 10/1988 Farmer et al. .................. 264/43
4,818,537 4/1989 Guo .................. 424/427

FOREIGN PATENT DOCUMENTS 0190926 8/1986 European Pat. Off. .

Primary Examiner—Thurman K. Page
Assistant Examiner—G. S. Kishore
Attorney, Agent, or Firm—Burns, Doane, Swecker & Mathis

[57] ABSTRACT

The invention relates to hemoglobin-containing liposomes in which an aqueous solution of hemoglobin is incorporated comprising liposome membrane mainly composed of hydrogenated phospholipids of hydrogenation ratio of 50% or more and an aqueous hemoglobin solution containing hemoglobin in a concentration of 30-60% (w/v). The method of preparation involves dissolving liposome membrane-forming lipids in an organic solvent, removing the solvent from said solution, adding an aqueous hemoglobin solution to the residue, subjecting the mixture to a shaking or an ultrasonication to give a uniform suspension, applying gas pressure to said suspension to allow said gas to permeate throughout said suspension and then subjecting said suspension to high pressure-delivery through fine openings. It is preferred that viscosity of the aqueous solution is $10^2$–3,000 cP (20° C.) and the inert gas pressure is 80–130 kg/cm².

11 Claims, 2 Drawing Sheets

LIPOSOME ENCAPSULATED HEMOGLOBIN

TECHNICAL FIELD

The present invention relates to a novel method for preparing liposomes. More particularly, the invention is concerned with a method for preparing liposomes with an aqueous solution innerly incorporated.

Furthermore, the invention relates to novel hemoglobin-containing liposomes (called hemosomes herein below) with a highly concentrated aqueous solution of hemoglobin innerly contained.

Liposomes are closed vesicles consisting of lipid bilayers with aqueous spaces innerly contained. Biological membranes are believed to be of lipid bimolecular structure. In this respect, liposomes are widely used in the study on physicochemical properties of the biomembrane as a model membrane. Various substances can be incorporated in aqueous spaces or in phospholipid bilayers of liposomes. The liposomes are fused with or incorporated in the cells so that they are also used as a carrier for delivering a substance into the living body. Studies using liposomes cover a wide variety of fields including biology, medical science and pharmaceutical science. Studies have been made on its application as a carrier for delivering oxygen or an anticancer drug, immunological application, cell interaction or application as a drug delivery system, etc.

Moreover, hemosomes are expected to be useful as artificial erythrocytes having high oxygen carrying capacity and safety and being stable to oxidation.

BACKGROUND TECHNOLOGY

As described above, liposomes are utilized in a wide variety of fields. However, it was impossible by the prior-art methods for preparing liposomes to produce liposomes with a high-viscosity aqueous solution innerly incorporated. Prior methods for preparing liposomes include so-called film methods, detergent-removal methods and reverse-phase evaporation methods. The film methods comprises forming a dried thin film of liposome-forming lipids on the inner surface of a vessel, to which an aqueous solution of a substance to be incorporated is added and subjecting the resulting mass to shaking or ultrasonication. The detergent-removal method depends upon removing detergents by dialysis from an aqueous solution which contains detergents and phospholipids to form mixed micelles, which results in the formation of liposomes. The reverse-phase evaporation method is a method in which liposomes are prepared by adding to an organic solvent solution of liposome-forming lipids an aqueous solution of a substance to be incorporated to form a water-in-oil emulsion and then removing the organic solvent by evaporation. According to these prior art methods, whereas liposomes are formed in cases where the aqueous solution to be innerly incorporated is of a low viscosity, the yield will be extremely low if it is of a high viscosity over 10 cP (20° C.), and desirable liposomes will not be produced in some cases. This has restricted uses of liposomes. For example, liposomes containing an aqueous hemoglobin solution are known as artificial erythrocytes, but, because of the viscosity restriction, the hemoglobin concentration cannot be so high as that of natural hemoglobin (which is 35% (w/v)), being as low as approximately 15%, so that the oxygen-carrying capacity is low.

On the other hand, Miller et al. reported a hemoglobin-containing liposome prepared by the so-called film method (U.S. Pat. No. 4,133,874). According to the method, the liposome is produced by dissolving liposome-forming lipids in an appropriate solvent such as chloroform, distilling off the solvent from the resulting solution to form a film of the lipids, to which an aqueous solution of hemoglobin is added and then subjecting the liposome to ultrasonication. The method, is advantageous in that the hemoglobin can be kept with relatively little degradation due to contact with oxygen only for a short period. However, the oxygen-carrying function is likely to be lost due to slow oxidation of the heme iron of hemoglobin in the liposome during storage. Although hemoglobin in the blood cell is provided with a mechanism wherein the hemoglobin oxidized to the methemoglobin is reduced to the original form by the action of enzymes, such mechanism is not workable if removed outside the blood cell by hemolysis so that the oxygen-carrying capacity is lost once denatured to the methemoglobin.

Hemoglobin is a macromolecular substance having a molecular weight of about 65,000 the aqueous solution of which has a high viscosity. According to the prior methods liposomes containing an aqueous solution with such a high molecular weight and viscosity cannot be prepared, and there are obtained liposomes containing hemoglobin in concentration as low as about 15%. As compared with the hemoglobin concentration of about 35% in natural erythrocytes, the above-cited concentration is not high enough for carrying oxygen. In order to provide a oxygen-carrying capacity equal to that of blood, the concentration of the hemosome itself cannot be increased, which will increase the concentration of the membrane-forming lipid material and induce a safety problem. Furthermore, viscosity of the lipid suspension will become so high that the dynamics blood flow will unfavorably be affected. Under such circumstances, liposomes innerly containing hemoglobin in a higher concentration are desirable.

The above-mentioned object is achieved by the present invention a described below.

SUMMARY OF THE INVENTION (1) A method for preparing liposomes which comprises dissolving liposome membrane-forming lipids in an organic solvent, removing the solvent from said solution, adding an aqueous solution to the residue, subjecting the mixture to shaking or ultrasonication to give an uniform suspension, applying gas pressure to said suspension to allow said gas to permeate throughout said suspension and then subjecting said suspension to high pressure-delivery through fine openings.

(2) A method according to item 1 wherein viscosity of the aqueous solution is 10–3,000 cP (20° C.).

(3) A method according to item 1 wherein the gas is an inert gas.

(4) A method according to item 1 wherein the inert gas is applied at a pressure of 80–130 kg/cm$^2$.

(5) A method according to item 3 wherein the suspension is subjected to a high pressure-delivery treatment using a gas-pressurizing high pressure-delivery emulsifier.

(6) A hemoglobin-containing liposome in which an aqueous solution of hemoglobin is incorporated comprising a liposome membrane mainly composed of hydrogenated phospholipids having a hydrogenation percentage of 50% or more and an aqueous hemoglobin solution containing hemoglobin in a concentration of 30-60% (w/v).

(7) A hemoglobin-containing liposome according to item 6 wherein the hydrogenated phospholipids are hydrogenated natural phospholipids.

(8) A hemoglobin-containing liposome according to item 7 wherein the hydrogenated natural phospholipids are hydrogenated lecithins.

(9) A hemoglobin-containing liposome according to item, 8 comprising hydrogenated lecithin having a hydrogenation percentage of 80% or more.

(10) A hemoglobin-containing liposome according to item 9 comprising hydrogenated phosphatidylcholine having a percentage of hydrogenation of 80% or more.

(11) A hemoglobin-containing liposome according to item 6 wherein the hemoglobin concentration is 50% (w/v).

(12) A hemoglobin-containing liposome according to any of the items 6-10 wherein the liposome membrane contains a negative charge-providing substance.

(13) A hemoglobin-containing liposome according to item 12 wherein the negative charge-providing substance is phosphatidic acid, dicetyl phosphate or a higher fatty acid.

DETAILED DESCRIPTION OF THE INVENTION

Figure 1:
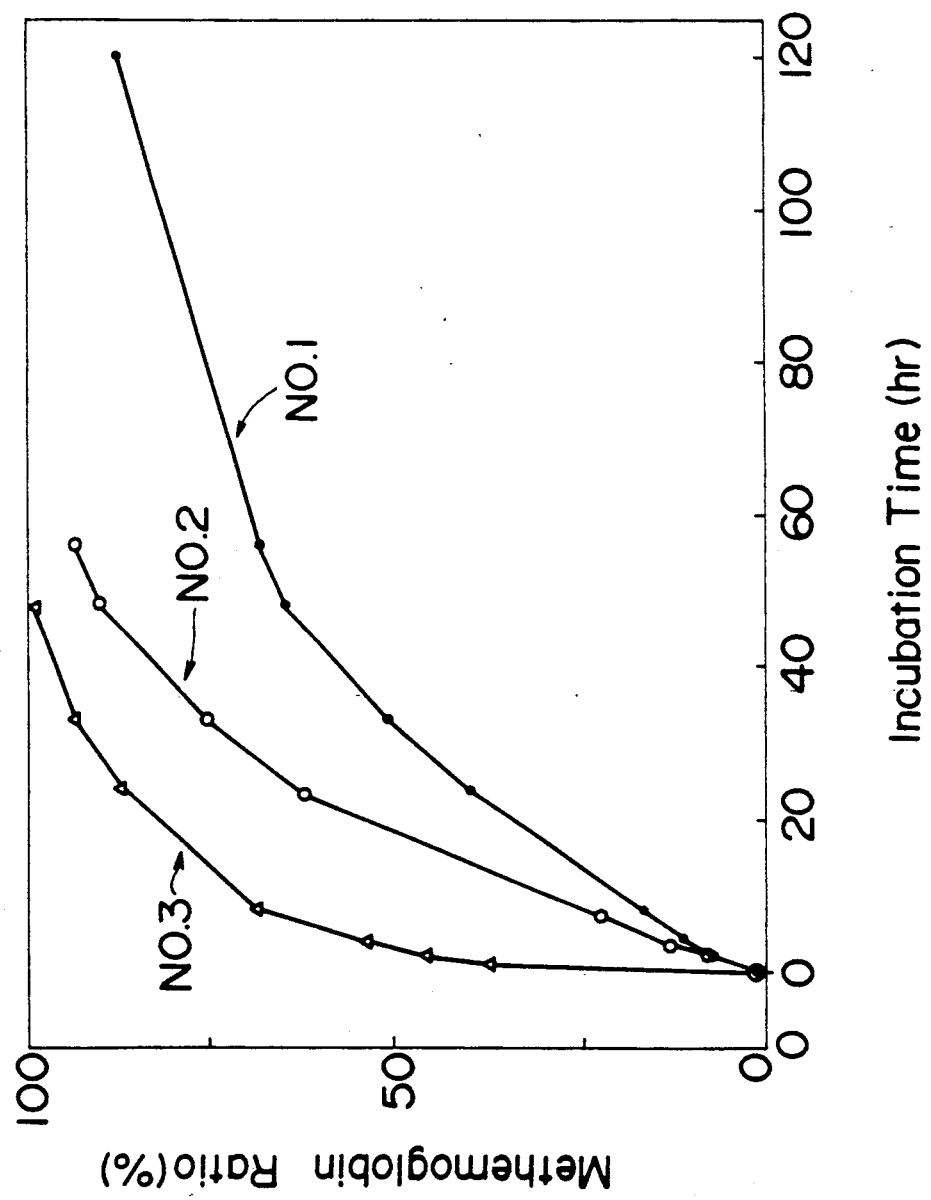
FIG. 1 is a graph indicating change with time of methemoglobin ratio (%) in the hemosomes.

There is no particular limitation on the liposome membrane-forming lipids, and any natural or synthetic lipids that form liposomes may be used. Especially preferred are phospholipids. As examples are mentioned lecithins, phosphatidylethanolamine, phosphatidic acid, phosphatidylserine, phosphatidylinositol, phosphatidylglycerol, sphingomyelin, cardiolipin and their hydrogenation products prepared by a conventional method. Their combination may also be employed. To the liposome membrane constituent may be added a membrane structure-reinforcing agent such as sterols and a disintegration time-controlling agent of an electric charge-providing substance (for example, stearic acid, oleic acid, linolic acid, linoleic acid, phosphatidic acid and phosphatidylglycerol). There is no particular limitation on the high viscosity-aqueous solution to be innerly incorporated in liposomes, and an aqueous solution of any chemical substance may be used. As examples of the chemical substance are mentioned, in addition to hemoglobin as described above, macromolecular compounds such as 8-glucuronidase, heparinase and β-glucosidase.

The viscosity of the aqueous solution is determined in accordance with the use of liposomes and depending upon nature of the solute. An aqueous solution having a viscosity in the range of 10 cP-3,000 cP (20° C.) is usually employed in the invention. Although an aqueous solution having a viscosity of 10 cP or below (20° C.) may be used in the invention, it can also be used in the prior-art preparative methods. For preparation of artificial erythrocytes, an aqueous solution of hemoglobin in a concentration of 30-60% (w/v) is preferably employed with the viscosity of 10-3,000 cP (20° C.).

The liposomes of the invention are prepared by dissolving liposome membrane-forming lipids in an organic solvent, removing the solvent from said solution, adding an aqueous solution to the residue, subjecting the mixture to shaking or ultrasonication to give a uniform suspension, applying gas pressure to said suspension to allow said gas to permeate throughout said suspension and then subjecting said suspension to high pressure-delivery through fine openings.

The steps up to preparation of an uniform suspension in the above-described method is the same as in the previously-mentioned method for preparing liposomes known as the film method, and are carried out by procedures known per se. The organic solvent is selected for specific applications of liposomes, and is usually chloroform, ethanol or the like.

It is preferable to use an inert gas such as nitrogen or argon as the gas used for pressure application when the aqueous solution contains a substance likely to degrade or when hydrogenation of the phospholipids is low.

Pressure is applied to the suspension thus obtained in a pressure vessel equipped with a nozzle of fine openings by an inert gas (for example, nitrogen or argon). Adequate pressure is 80-130 kg/cm$^2$ After the inert gas has been thoroughly permeated through the suspension, the suspension is subjected to a delivery treatment from the nozzles.

The step for high pressure-delivery treatment of the suspension is carried out by delivering the suspension once or several times through the openings by means of a high pressure delivery emulsifier, preferably a gas-pressurizing high pressure-delivery emulsifier while maintaining the above-mentioned pressure. In this step, the suspension through which the inert gas has been permeated is vigorously emulsified by rapid expansion of the gas under pressure to form liposomes. Higher pressure delivery produces liposomes of smaller particle sizes. Unheld materials are washed out of the liposomes thus obtained by a conventional method, and the liposomes are isolated by ultracentrifugal treatment or the like.

It is noted that the gas-pressurizing high pressure-delivery emulsifier used in the invention comprises an usual gas bomb or a high pressure gas supplier and a pressure vessel equipped with a fine-opening nozzle, the pressure vessel being provided in communication with said gas bomb or high pressure gas supplier. Since the principle is simple, the method can be widely applied to various scales from a small production to industrial one by using a pressure vessel corresponding to the amount to be treated. Also, the use of few mechanical parts are advantageously associated with little troubles.

The membrane material of the hemosomes according to the invention is mainly composed of hydrogenated phospholipids having a percentage of hydrogenation of 50% or more.

The fatty acid composition of natural phospholipids, obtained from soybean, egg yolk and others contain a lot of unsaturated fatty acid chains. In the present invention, hydrogenated phospholipids in which 50% or more of unsaturated fatty acid chains of the natural phospholipid, as mentioned above, being saturated with hydrogen are preferably used.

Synthetic distearoyllecithin is stable to oxidation due to the absence of unsaturated fatty acids in the molecule but is inferior in the trapping of hemoglobin compared to hydrogenated natural lecithins. It is believed that while hydrogenated phospholipids are a mixture of phospholipids containing in the molecule various fatty acids, synthetic distearoyllecithin is a single compound containing as the fatty acid stearic acid alone.

The percentage of hydrogenation in the hydrogenated phospholipids used in the invention is 50% or more, preferably 80% or more and is, in terms of the iodine value, not more than 30, preferably not more than 10. A percentage of hydrogenation less than 50% will be insufficient for the prevention of hemoglobin oxidation. As examples of the hydrogenated phospholipid are mentioned hydrogenation products of lecithins, phosphatidylethanolamine, phosphatidylinositol, phosphatidylserine, phosphatidylglycerol, sphingomyelin, cardiolipin and the like produced by a conventional method. Particularly preferred are hydrogenated natural lecithins produced by hydrogenation of soybean lecithin, egg yolk lecithin, corn lecithin, cotton seed oil lecithin, rape oil lecithin, etc.

The percentage of hydrogenation is determined as follows: The fatty acid chains of hydrogenated phospholipids are converted to their methyl esters by the method of Jhum et al. (J. Am. Oil Chem. Soc. 53, 132 (1982)] and then analyzed by GLC for calculation of the iodine value from the composition of fatty acids. The iodine value of the unhydrogenated phospholipid is determined in the same way as above, and the percentage of hydrogenation is calculated from the percent of the latter to the former iodine value of hydrogenated phospholipids.

To the membrane material of the hemosomes according to the invention may be added a sterol such as cholesterol or cholestane in order to reinforce the membrane. Also in order to prevent aggregation of the liposome a negative charge-providing substance, for example, phosphatidic acid, a higher fatty acid or dicetyl phosphate may be added. In addition, when an antioxidant such as tocopherol (vitamin E) is added to the membrane material, oxidation of the liposome membrane is inhibited.

For example, tocopherol may be added in a proportion of 0.01-0.1 mol, preferably 0.04 mol per mol of phospholipids.

As the hemoglobin to be innerly incorporated in the liposomes is used a product obtained by hemolyzing erythrocytes according to a conventional method followed by ultrafiltration using a membrane for fraction-ation of molecular weights of 50,000 and below to a concentration of 30% (w/v) or higher. Hemoglobin is incorporated into liposomes in an aqueous solution in a concentration of 30-60% (w/v), the viscosity being approximately 10-3,000 cP (20° C.).

The hemosomes of the invention are prepared by dissolving a liposome membrane material mainly composed of the above-described hydrogenated natural phospholipid in an organic solvent, removing the solvent from said solution, adding an aqueous solution of hemoglobin in a concentration of 30-60% (w/v) to the residue, subjecting the mixture to shaking or ultrasonication to give on uniform suspension, applying pressure by inert gas to said suspension to allow the inert gas to permeate throughout said suspension and then subjecting said suspension to high pressure-delivery through fine openings.

Steps up to the preparation of the homogeneous suspension in the above-described preparative method is the same as in the liposome-preparative method known as the film method as mentioned above except for the use of a membrane material mainly composed of hydrogenated natural phospholipids. These steps are carried out by procedures known per se. As the organic solvent are usually employed chloroform, ethanol and the like.

The suspension thus obtained is treated by the above-described high pressure-delivery method, which is washed by a conventional method and subjected to an ultracentrifugal treatment to afford the desirable hemosomes.

The invention will be described in more detail with reference to examples and test examples.

EXAMPLE (1) Preparation of stroma-free hemoglobin (SFH) solution

Using a blood-collecting pack containing an anticoagulant, 15 lit. of whole bovine blood is collected from the vein. The collected whole blood is aseptically transported and stored in a closed vessel at 4° C. All of the subsequent steps are carried out aseptically at a low temperature.

Centrifugal washing is effected with a physiological salt solution by means of a continuous centrifuge thereby producing 5 lit. of crude washed erythrocytes in which platelets, leucocytes and plasma have been removed.

Further washing is carried out with physiological salt solution by means of a plasma separator 0.45 $\mu$ in pore diameter. Hemolysis is attained by using 10 lit. of pyrogen-free distilled water per 5 lit. of the washed erythrocytes. Removal of the erythrocyte membrane and filtration sterilization are conducted by means of a plasma separator 0.45 $\mu$m in diameter and a plasma component separator 0.1 $\mu$m in diameter, respectively. There is obtained approximately 12 lit. of stroma-free hemoglobin in a hemoglobin concentration of 8% (w/v).

Ultrafiltration using a dialyzer for dialysis TAF10W (a cellulose hollow dialyzer manufactured by Terumo Corporation) gives approximately 1.8 lit. of stroma-free hemoglobin (SFH) solution in a hemoglobin concentration of 50% (w/v).

(2) Preparation of liposome-forming lipids

In chloroform are dissolved 27.76 g of purified egg yolk phosphatidylcholine having a percentage of hydrogenation of 80%, 6.96 g cholesterol and 3.75 g of purified phosphatidic acid having a percentage of hydrogenation of 80%. Said lipid solution is placed in a round-bottom flask and subjected to evaporation to remove the chloroform, thereby forming the lipid membrane at the bottom of the flask. Further, vacuum drying is conducted for 16 hours to completely remove the chloroform.

(3) Preparation of SFH-lipid mixture

To said lipid membrane is added 300 ml of the 50% SFH obtained in the above SFH preparative step. The mixture is subjected to shaking or ultrasonication to give a uniform suspension, which is used as the starting material.

(4) Preparation of hemoglobin-containing liposomes by pressure delivery with inert gas Said starting material is placed in a Parr Cell Disruption Bomb (manufactured by Parr Instrument Company, USA) which is a pressure vessel with a fine-opening nozzle, and pressurized at 130 kg/cm$^2$ by introducing nitrogen gas. The nitrogen gas is thoroughly permeated through the starting material by standing for 30 min. Then the valve of the nozzle is slowly opened to deliver the starting material while maintaining the pressure at 130 kg/cm².

(5) Purification of hemoglobin-containing liposomes

The material after the delivery is ten times diluted with physiological salt solution and centrifuged (17,000 rpm, 30 min.) to separate hemoglobin-containing liposome precipitates. The hemoglobin in the supernatant that has not participated in the capsulation is removed by decantation. Then, the hemoglobin-containing liposome precipitates are suspended in a physiological salt solution, and the suspension is again centrifuged. The same procedures are repeated until no hemoglobin is detected in the supernatant.

(6) Removal of coarse particles

The suspension of the hemoglobin-containing liposomes after the purification is filtered through a porous polycarbonate filter 0.4 μ in pore diameter (manufactured by Nuclepore Corporation, USA) to remove coarse particles.

(7) Adjustment of hemoglobin concentration

There was obtained 180 ml of a suspension in a physiological salt solution adjusted to a hemoglobin concentration of 10%.

Yield of the hemoglobin at this stage was $$\frac{\text{Final hemoglobin concentration} \times \text{Volume of liquid artificial erythrocytes (ml)}}{\text{SFH concentration} \times \text{Added amount of SFH (ml)}} \times 100\% =$$

$$(10 \times 180/50 \times 300) \times 100 = 12\%.$$

TEST EXAMPLE 1

Oxidation of hemoglobin

The hydrogenated phospholipid hemosomes prepared in Example (No. 1), non-hydrogenated phospholipid hemosomes (containing vitamin E) (No. 2) and non-hydrogenated phospholipid hemosomes (containing no vitamin E) (No. 3) were respectively suspended in a physiological salt solution and allowed to stand at 37° C. Ratio of methemoglobin (%) was then measured with the passage of time.

Results are shown in FIG. 1. As clearly seen in FIG. 1, the oxidation (metho conversion) preventive effect is observed with the hydrogenated phospholipid hemosomes of the invention (No. 1).

Test Example 2

The lipid concentration-decreasing effect of the conversion of a concentrated aqueous solution of hemoglobin to liposomes on hemoglobin concentration in the hemosome suspension was examined.

Ratio of lipid concentration in the hemosome suspension: L (mg/ml) to hemoglobin concentration: H (mg/ml) in the 50% SFH hemosome prepared in Example (No. 1), a hemosome prepared from 30% (w/v) SFH (No. 4) and a hemosome prepared from 15% (w/v) SFH (No. 5) respectively as control, namely, L/H is shown in Table 1.

TABLE 1

| Sample | | L/H |
| --- | --- | --- |
| No. 1 | 50% SFH hemosomes | 1.29 |
| No. 4 | 30% SFH hemosomes | 3.48 |

TABLE 1-continued

| Sample | | L/H |
| --- | --- | --- |
| No. 5 | 15% SFH hemosomes | 6.76 |

As shown in Table 1, the effect of decrease in lipid concentration on Hb concentration is clearer as SFH concentration increases.

TEST EXAMPLE 3

Effect of the conversion of a concentrated aqueous hemoglobin solution to liposomes on decrease in the viscosity of a hemosome suspension was examined.

The viscosity of 50% SFH hemosome suspension (No. 1), SFH hemosome suspension (No. 4) and 15% SFH hemosome suspension (No. 5), respectively, were examined when hemoglobin concentration in the hemosome suspension (physiological salt solution) was kept constant (7%). Results are shown in FIG. 2.

Figure 2:
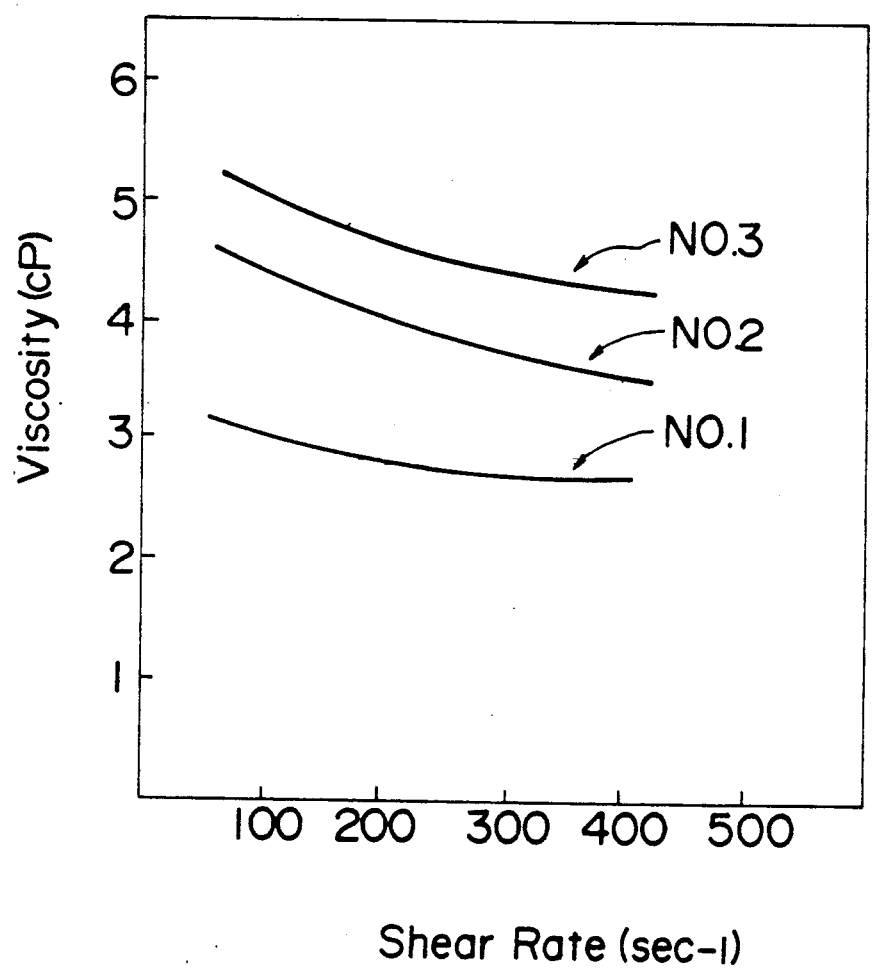
FIG. 2 is a graph indicating viscosity of the hemosome suspension.

It is clear from FIG. 2 that when the viscosity is compared at a constant hemoglobin concentration in the hemosome suspension, the higher the content of SFH the greater decrease in the viscosity of the hemosome suspension.

COMPARATIVE EXAMPLE

The SFH-lipid suspension prepared in Example (Stage 3 in the example) was treated with a French press (Ohtake Seisakusho) The same effect as in the Example was searched with reference to the particle size. Whereas one treatment under a pressure of 200 kg/cm² formed liposomes, the particle size was irregular. Five treatments were needed in order to produce the same particle size as in the Example. The same procedures as in and after Stage 5 in the Example also afforded 154.5 ml of artificial erythrocytes. The yield was $$[10 \times 154.5 \text{ (ml)} / 50 \times 300 \text{ (ml)}] \times 100 \text{ (\%)} = 10.3\%,$$

which yield was also inferior as compared with the Example. Operation time was also found shorter in the Example.

What is claimed is:

1. A hemoglobin-containing liposome in which an aqueous solution of hemoglobin is incorporated comprising a liposome membrane composed of a hydrogenated phopholipid having a percentage of hydrogenation of 50% or more and an aqueous hemoglobin solution containing hemoglobin in a concentration of 30-60% (w/v).

2. A hemoglobin-containing liposome according to claim 1 wherein the hydrogenated natural phospholipids are hydrogenated lecithin.

3. A hemoglobin containing liposome according to claim 2 comprising hydrogenated lecithin having a percentage of hydrogenation of 80% or more.

4. A hemoglobin-containing liposome according to claim 3 comprising hydrogenated phosphatidylcholine having a percentage of hydrogenation of 80% or more.

5. A hemoglobin-containing liposome according to claim 1, wherein the hemoglobin concentration is 50% (w/v).

6. A hemoglobin-containing liposome according to claim 5 wherein the negative charge-providing substance is phosphatidic acid or dicetyl phosphate.

7. A hemoglobin-containing liposome in which an aqueous solution of hemoglobin is incorporated comprising a liposome membrane composed of a hydrogenated phospholipid having 50% or more hydrogenation and an aqueous hemoglobin solution containing hemoglobin in a concentration of 30-60% (w/v) prepared by dissolving liposome membrane-forming lipids in an organic solvent, removing the solvent form said solution thereby leaving a residue, adding an aqueous solution to the residue, subjecting the mixture to shaking or ultrasonication to give an uniform suspension, applying gas pressure to said suspension to allow said gas to permeate throughout said suspension and then subjecting said suspension to high pressure-delivery through fine openings.

8. A hemoglobin-containing liposome according to claim 7 wherein viscosity of the aqueous solution is 10-3,000 cP (20° C.).

9. A hemoglobin-containing liposome according to claim 7 wherein the gas is an inert gas.

10. A hemoglobin-containing liposome according to claim 7 wherein the inert gas is applied at a pressure of 80-130 kg/cm$^2$.

11. A hemoglobin-containing liposome according to claim 7 wherein the suspension is subjected to a high pressure-delivery treatment using a gas-pressurizing high pressure-delivery emulsifier.

* * * * *